United States Patent [19]

Soltz et al.

[11] Patent Number: 5,272,716
[45] Date of Patent: Dec. 21, 1993

[54] HAND HELD LASER APPARATUS

[75] Inventors: Barbara A. Soltz, Spring Valley, N.Y.; Charles R. Chubb, St. Peters, Mo.; James D. Cook, Freeport, Ill.; Thomas M. Pallett, III, Florissant, Mo.; Richard G. Podgornik; Dale F. Waldo, both of St. Louis, Mo.

[73] Assignee: McDonnell Douglas Corporation, St. Louis, Mo.

[21] Appl. No.: 775,428

[22] Filed: Oct. 15, 1991

[51] Int. Cl.⁵ .................................................. H01S 3/00
[52] U.S. Cl. .......................................... 372/109; 372/6; 372/29; 372/38; 219/121.6
[58] Field of Search ................ 372/109, 29, 38, 6; 219/121.6

[56] References Cited

U.S. PATENT DOCUMENTS

| 4,665,529 | 5/1987 | Baer et al. | 372/109 |
| 4,757,515 | 7/1988 | Hughes | 372/109 |
| 4,808,789 | 2/1989 | Mucheryan | 219/121.6 |
| 4,926,438 | 5/1990 | Maes et al. | 372/109 |

FOREIGN PATENT DOCUMENTS 0007178  1/1987  Japan .................................. 372/109

Primary Examiner—Georgia Y. Epps
Attorney, Agent, or Firm—Guy R. Gosnell; Benjamin Hudson, Jr.; Timothy H. Courson

[57] ABSTRACT

A hand held laser apparatus containing a semiconductor laser diode switchably connected to a power supply. The output of the laser diode is focused and collimated by a pair of lens. Circuitry is provided to allow for either continuous wave or pulsed modes of operation as well as the capability of varying the pulsewidth of the laser. A guide laser or a light emitting diode is provided to guide the operator. The power level of the guide laser is limited so that it transfers minimal power to the workpiece but provides a visible line of laser light along which the output of the semiconductor laser diode will travel. A photodetector may be positioned between the laser diode and the lenses. Additionally, the amount of current delivered to the laser in continuous wave mode of operation or the pulse width and duty cycle of a pulse may be measured and displayed. Embodiments are provided incorporating a plurality of laser diodes to allow continued operation upon failure of a diode, increased power with the simultaneous use of the multiple diodes, or either alternate wavelength selection or wavelength mixing. Alternative embodiments operate at a predetermined voltage level. These embodiments may utilize a set of batteries such that the entire batteries and control circuitry may be contained either within a portable package or the hand held laser apparatus itself. Such alternative embodiments may be made so as to be disposable upon the discharge of their batteries or the exhaustion of the laser.

19 Claims, 3 Drawing Sheets

HAND HELD LASER APPARATUS

BACKGROUND OF THE INVENTION

This invention relates generally to hand held laser apparatuses and more particularly to hand held laser apparatuses for directly delivering a high power output in either a continuous wave or a pulsed mode of operation to a workpiece by means of a lens assembly or a combination of a lens assembly and fiber optic assembly.

In many applications, such as the medical field and industrial processing, it is desirable to position and direct a beam of laser light to a target through the manipulation of a hand held device. By utilizing a hand held device the operator may obtain a more precise location of the laser light and be able to rapidly alter its position as conditions warrant. Typically, large laser generators, such as a Nd:YAG laser generator or a $CO_2$ laser generator, have been utilized wherein these relatively large laser generators are coupled to a mobile hand piece by means of fiber optic cabling. Thus, by correctly orientating the hand piece, the light generated by the laser generator could be applied to the workpiece. The use of such large laser generators, however, suffered from several deficiencies. One such deficiency is the need to house and maintain the relatively large laser generator as well as the requirement that it is positioned within a fairly short distance from the sight of the laser's utilization due to the desire to minimize problems with the fiber optic coupling. Additionally, such laser generators performed relatively inefficiently in comparison to modern semiconductor laser diodes.

It is also desirable that such hand held laser apparatuses be able to provide both continuous wave and pulsed modes of operation since the various applications to which the hand held laser apparatuses could be applied may required varying operating characteristics by the laser. For example, in the medical field the various applications of the hand held laser apparatus such as photocoagulation, tissue welding, photodynamic therapy, contact surgery and tissue ablation each typically require different operating characteristics by the laser in order to most efficiently perform the desired medical function. Additionally, for a hand held laser apparatus operating in a pulsed mode, it would be desirable that the pulsewidth as well as the repetition rate of the pulses be variable so as to optimize the laser's pulses for the application to which it is applied.

Additionally, for a hand held laser apparatus wherein the laser diode itself is contained within the hand held apparatus, it would be desirable for the output of the laser diode to be directed upon the workpiece without the need for fiber optic coupling. By applying the laser beam directly to the workpiece without the use of fiber optic coupling, problems inherent in the use of coupling the laser output to the fiber optic cable in its transmission therethrough are avoided. Furthermore, it is desirable to have the power level of the hand held laser device be variable to accommodate various applications of the apparatus as well as providing a means detecting the output power so that manual adjustment could be made in the case of an errant power output.

SUMMARY

There is provided by this invention a hand held laser apparatus wherein the hand held laser apparatus itself contains the semiconductor laser diode. The laser diode within the hand held laser apparatus is switchably connected to a power supply which may be external to the hand held laser apparatus. The output of the laser diode is focused and collimated by a pair of lens such that sufficient transfer of its power is provided to the workpiece upon which the output of the hand held laser apparatus is directed.

Additionally, circuitry is provided to allow for either continuous wave or pulsed modes of operation as well as the capability of varying the pulsewidth of the laser to accommodate various application of the hand held laser apparatus. A guide laser or a light emitting diode is provided within the hand held laser apparatus as well to serve to guide the operator of the hand held laser apparatus in his application of the semiconductor laser diode to the workpiece. The power level of the guide laser is limited so that it transfers minimal power to the workpiece but provides a visible line of laser light along which the output of the semiconductor laser diode will travel.

A photodetector may also be positioned between the semiconductor laser device and the lenses for providing a signal indicative of the output power level of the laser device. This signal may be displayed for the operator who may then adjust the input power supplied by the power supply should the output be different than that desired. Additionally, the amount of current delivered to the laser in continuous wave mode of operation or the pulse width and duty cycle of a pulse may be measured and displayed for the operator.

An embodiment is also provided wherein the output of the photodetector is compared to a predetermined power level. Should the output fall below the preset value, the first semiconductor laser device is disconnected from the power supply while a second semiconductor laser device, with its associated control circuitry, is connected via a switch to a power supply. In this fashion, output power level of constant power may be obtained even should the first semiconductor laser or its associated circuitry should fail.

Alternative embodiments are provided which are designed to operate at a predetermined voltage level. The alternative embodiments may utilize a set of batteries such that the entire batteries and control circuitry may be contained either within a portable package or the hand held laser apparatus itself. Such alternative embodiments may be made so as to be disposable upon the discharge of their batteries or the exhaustion of the laser.

Additionally, embodiments are provided which utilize a plurality of individual semiconductor laser devices or a semiconductor laser array. The multiple, individual semiconductor laser devices or the semiconductor laser array may be utilized simultaneously for increased power. Alternatively, with the use of multiple individual semiconductor lasers the lasers may be selected such that each laser will emit a different wavelength of light and be connected such that the operator could selectably energize one or more of the semiconductor lasers so that the apparatus would emit light of varying wavelength or light having a mixture of two or more wavelengths.

DETAILED DESCRIPTION OF THE PREFERRED EMBODIMENT

Figure 1:
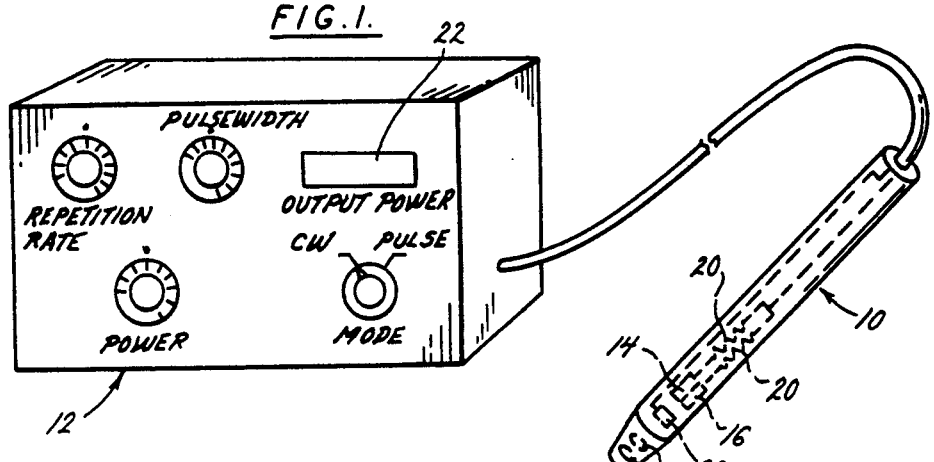
FIG. 1 is a perspective view of a hand held laser apparatus incorporating the features of this invention.
Figure 2:
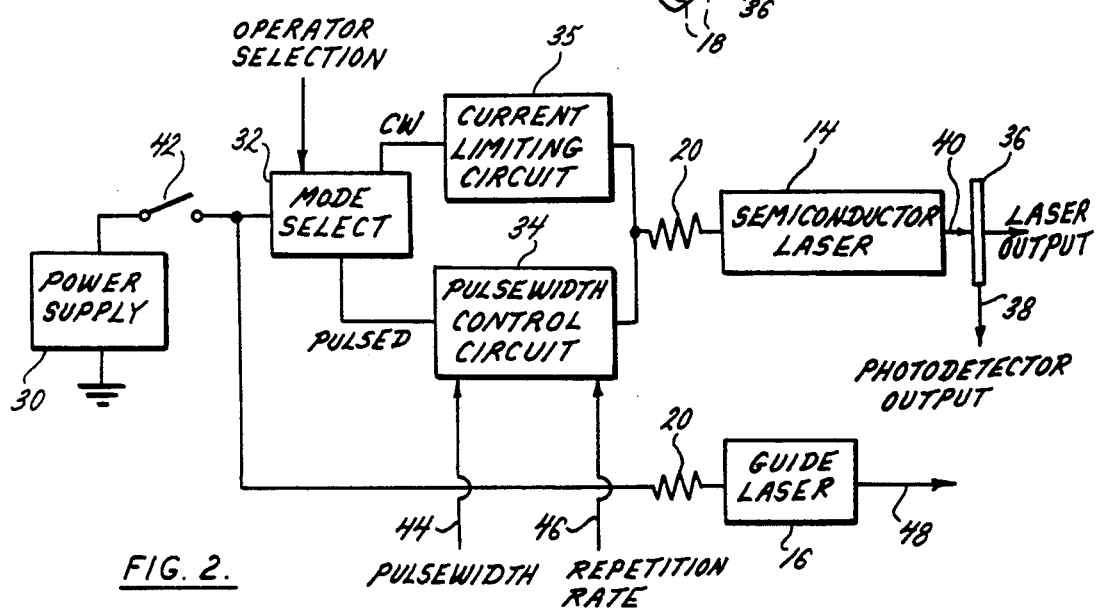
FIG. 2 is a block diagram representation of the power supply and control circuitry of the hand held laser apparatus.

Referring to FIG. 1, there is shown a hand held laser apparatus 10 and an external power supply 12 including control circuitry. A hand held laser apparatus generally comprises a semiconductor laser device 14, a guide laser device 16, and a pair of lens 18 for focusing and collimating the output of the laser devices. A pair of current limiting resistors 20 may also be introduced in the hand held laser apparatus 10 to protect the semiconductor laser devices. Within the power supply control circuit 12, as shown in FIG. 2, is a power supply 30 switchably connected to the semiconductor laser devices of the hand held laser apparatus 10. Additionally, the power supply control circuit 12 is comprised of a mode control circuit 32 and a pulsewidth control circuit 34. There may also be a photodetecting element 36 within the hand held laser apparatus 10, the output 38 of which is relayed to the power supply control circuit 12 which provides an output indicative of the semiconductor laser devices' output 40. In this fashion, the level of power supplied by the power supply 30 may be adjusted in order to alter the injection current of the semiconductor laser 14 and in turn to alter the output power 40 of the semiconductor laser device 14.

In FIG. 2, there is shown a block diagram representation of the circuitry required for the hand held laser apparatus 10. The power supply 30 may be any of those well known to those skilled in the art which is capable of being varied by an operator. The power supply 30 is switchably connected to the semiconductor laser device 14. The switching means 42 is typically a MOSFET switch. A resistive element 20 is introduced between the switching means 42 and each of the semiconductor laser device 14 and the guide laser device 16 in order to limit the current applied to the laser devices so as to protect those devices.

Figure 3:
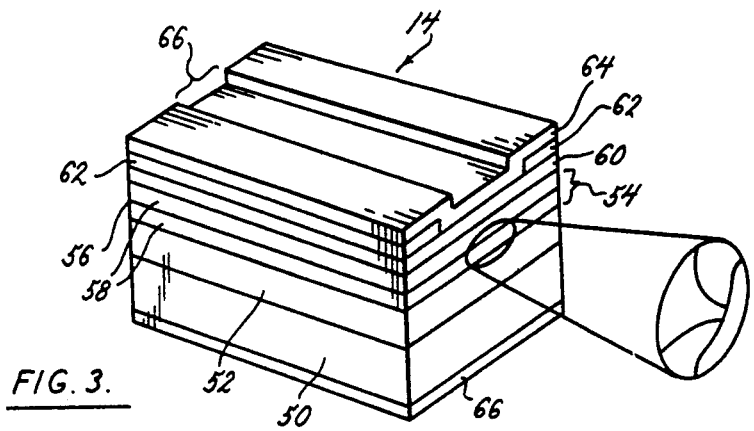
FIG. 3 is a perspective view of a semiconductor laser device for use in the hand held laser apparatus.

The semiconductor laser device 14 may be of any conventional design capable of delivering three watts of power and being focused to a location on a workpiece. Additionally, the semiconductor laser device 14 must be capable of operating in either a continuous wave or pulsed mode of operation. An exemplary semiconductor laser device 14 may be comprised, as shown in FIG. 3, of a GaAs substrate 50 upon which an N-doped AlGaAs cladding layer 52 is deposited. Upon the N-doped cladding layer 52 is typically formed a GRIN-SCH structure 54. In this GRIN-SCH structure 54, a single quantum well 56 of GaAs is formed as a thin layer between layers 58 of AlGaAs whose index of infraction varies as it proceeds from the cladding layer to the quantum well 56. Typically, the percentage of aluminum in the AlGaAs decreases from the percentage present in the cladding layer as the quantum well 56 is approached. Deposited on top of the GRIN-SCH structure 54 is a P-doped AlGaAs cladding layer 60. Upon the P-doped cladding layer 60 is deposited an oxide cap layer 62 typically comprised of silicon dioxide. A stripe or rib 66 of the oxide cap layer 62 is thereinafter removed by etching processes familiar to those skilled in the art. A P-contact layer 64, typically comprised of P-doped GaAs, is thereinafter deposited upon the etched oxide cap layer 62. Furthermore, on the substrate 50, an N-contact layer 66 is deposited typically comprised of N-doped GaAs. Thus, a semiconductor laser device 14, as the one previously described, will produce an output in the portion of the quantum well region 56 which lies beneath the stripe 66 etched from the oxide layer 62 when a sufficient voltage difference is maintained between the N- and P contact layers, 66 and 64 respectively. Typically, the N-doping is provided by selenium and the P-doping by zinc, however, other materials may be utilized as well known to those skilled in the art.

As shown in FIG. 2, there is also provided a mode select circuit 32 for the operator of hand held laser apparatus 10 to select either continuous wave or pulsed laser operation. If continuous wave operation is selected, an uninterrupted current is supplied by the power source 30 to the semiconductor diode laser 14 such that a continuous wave of laser output 40 is produced by the semiconductor laser device 14. Typically, if a continuous wave mode is selected the laser is protected against excessive current by a current limiting circuit 35 as shown in FIGS. 2 and 4.

Figure 4:
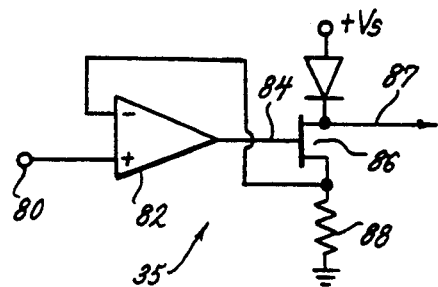
FIG. 4 is a circuit diagram of the current limiting circuitry of the hand held laser apparatus.

While the current limiting circuit 35 may be comprised of any combination of elements which effectively limit the current provided to the laser, an exemplary configuration is shown in detail in FIG. 4. Typically, the signal 80 provided by the power source, which has been previously scaled such that the desired output power-level of the semiconductor laser 14 is attained, is input to a positive terminal of an operational amplifier 82. The output 84 of the operational amplifier 82 is connected to the gate terminal of a field effect transistor 86 which, based upon the voltage provided by the operational amplifier's output 84, produces a drain current 87 in the transistor 86 which, in turn, drives the semiconductor laser 14. A current sensing resistor 88, typically having a small resistive value such as 0.1 ohms, is connected between a source terminal of the transistor 86 and ground such that a portion of the current which is produced by the transistor 86 flows through the current sensing resistor 88. A negative terminal of the operational amplifier 82 is also connected to the source of the transistor 86 so that the voltage produced across the current sensing resistor 88 provides negative feedback to the operational amplifier 82 such that if the current supplied to the laser 14 becomes too large, the output 84 of the operational amplifier 82 will be decreased such that the laser 14 is protected from excessive current.

Alternatively, if a pulsed mode of operation is selected, current sufficient to produce a pulsed output from the semiconductor laser device 14 is provided by the power supply 30. If the pulsed mode of operation is selected, the pulsewidth 44 and repetition rate 46 of the pulses must also be selected by the operator.

Figure 5:
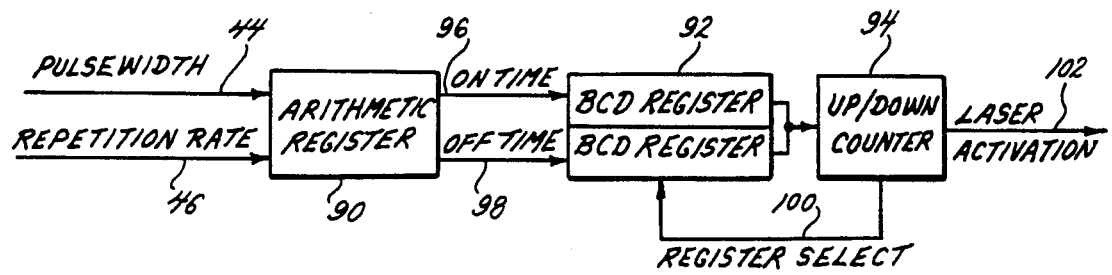
FIG. 5 is a block diagram of the pulsewidth control circuitry of the hand held laser apparatus.

As shown in FIGS. 2 and 5, the selections made by the operator, when the pulsed mode of operation is selected, are input to the pulsewidth control circuit 34. An exemplary design of the pulsewidth control circuit 34 is illustrated in FIG. 5 and is comprised of an arithmetic register 90, dual binary coded decimal (BCD) registers 92, and an up/down counter 94. The operator's selections of the desired pulsewidth 44 and repetition rate 46 are input to the arithmetic register 90 which has internal circuitry to translate the pulsewidth 44 and repetition rate 46 of the pulses into an on time 96 and an off time signal 98. The on time signal 96 is the length of time at which the pulse to be delivered is at a high state, while the off time signal 98 is the length of time at which the pulse is in a low state. The length of time stored by the on time signal 96 and off time signal 98 are represented in microseconds since the BCD registers 92 and up/down counter 94 are clocked by a 1 MHz clock, but may be represented in milliseconds or other units of time if an alternate clocking means is utilized.

The on time signal 96 and the off time signal 98 are each stored in one of the dual BCD registers 92. Upon the closing of the switch 42 to activate the hand held laser apparatus 10, the on time signal 96 is loaded in the up/down counter 94, which has been previously set to decrement the value loaded therein. The up/down counter 94 subsequently counts down the preloaded on time signal 96 and upon reaching zero signals the dual BCD register 92 to load the off time value 98 into the up/down counter 94. The up/down counter 94 then counts down the loaded off time value 98 as well. The register select signal 100 alternately selects the BCD register containing the on time signal 96 and the BCD register containing the off time signal 98 as the value previously loaded has been counted down to zero.

Additionally, the up/down counter 94 has a laser activation signal 102 which signals that the switch 42 is closed and provides sufficient current to cause the laser 14 to lase during the period of time in which the on time value 96 has been loaded and is being counted down by the up/down counter 94. Alternatively, the laser activation signal 102 provides a current which is less than the laser's threshold current so that the laser 14 does not produce an output during the period of time in which the off time value 98 has been loaded and is being counted down by the up/down counter 94.

Thus, as shown in block diagram form in FIG. 2, and previously described the pulsewidth control circuit 34 switchably controls the current supplied by the power source 30 such that current is only supplied to the semiconductor laser device 14 during the portion of a pulse when an output is desired while inhibiting flow of substantial current from the power supply 30 when the semiconductor laser device 14 is desired to be inactive. Additionally, pulses of the desired width are produced at an interval determined by the repetition rate 46 selected by the operator. In this way, a repetitive pulse of a desired pulsewidth is obtained from the semiconductor laser device 14.

Additionally, as shown in FIG. 2, the power supply 30 is switchably connected, typically by means of a MOSFET switch, to a guide semiconductor laser device 16. Interposed between the switching means 42 and the guide laser device 16 may be a resistive element 20 to limit the current so as to protect the guide laser device 16. The guide laser device 16 may be any of those semiconductor laser devices well known to those skilled in the art which produces a visible beam of laser light such as the visible light semiconductor laser device disclosed in U.S. Pat. No. 4,922,499. The current supplied to the guide laser 16 device is limited such that the power output by the guide laser device 16 is minimal such that it does not interfere with the operation of the semiconductor laser device 14 on the workpiece.

The output of both the semiconductor laser device 14 and the guide laser device 16 are focused and collimated by a pair of lenses 18 contained in the tip of the hand held laser apparatus 10. The output beams of both the semiconductor laser device 14 and the guide laser devices 16 are oriented so as to travel an identical linear path. In this fashion, an operator may locate the visible guide laser beam 48 and in doing so also position the output 40 of the semiconductor laser device 14 as he so desires.

As an alternative to a guide laser device, a light emitting diode (LED) may be utilized to illuminate the path which the semiconductor laser device will travel. The LED may be switchably connected, as explained in conjunction with the guide laser means, to the power supply. A resistive element may be interdisposed to protect the LED in a like manner to that previously discussed. The LED and the associated semiconductor laser device would each need to be focused and collimated by its own dedicated pair of lenses as distinguished from the use of a guide laser means which may utilize the same pair of collimating and focusing lenses as the semiconductor laser device.

While the hand held laser apparatus has been described and illustrated in conjunction with an external power supply which contains the control circuitry, the power supply and the control circuitry may be incorporated within the housing of the laser apparatus to enable the device to be more easily transported.

Additionally, while the hand held laser apparatus, as shown in FIG. 1, is packaged in a linear housing, the apparatus is able to be packaged in housings of varied configurations. An angled configuration 110 which may allow easier access for the operator in certain situations, such as those situations allowing little space for the introduction of an instrument, is shown in FIG. 6 in conjunction with a third embodiment of the hand held laser apparatus.

In a second embodiment, the output level 40 of the semiconductor laser device 14 may be set to a predetermined power level. In this case, an adjustable power supply in unnecessary and a power supply of a predetermined voltage level may be utilized. In this second embodiment, the power supply 30 may be a set of batteries which may be contained along with the control circuitry for the mode select 32 and the pulsewidth control 34 in a mobile package that may be attached to the operator such as by hooking it to the operator's waistband.

Figure 6:
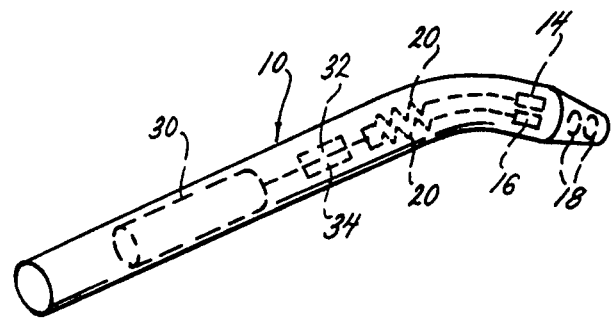
FIG. 6 is a hand held laser apparatus having an angle housing.

Such a mobile hand held laser apparatus 10 may also be embodied in a third embodiment, as shown in FIG. 6, which, like the second embodiment, is desired to operate at a predetermined power level. The third embodiment utilizes a hand held laser apparatus 10 in which the power supply 30, or batteries in this instance, as well as the control circuitry for the mode select 32 and the pulsewidth control circuitry 34 are all contained within the hand held laser apparatus 10 itself. In this fashion, a very mobile, and relatively inexpensive, hand held laser apparatus 10 is provided which is capable of operation in locations not accessible by electricity or with limited space in which to operate the apparatus.

The embodiment of the hand held laser apparatus 10 previously discussed may also be simplified if the apparatus 10 need only operate in one of the modes, continuous wave or pulsed. In this case the mode select circuitry 32 may be omitted and a direct connection may be provided from the switching means 42 to the semiconductor laser 14 for continuous wave operation or the switching means 42 may be connected to the semiconductor laser 14 via a pulsewidth control circuit 34 for pulsed operation. If a pulsed mode of operation has been permanently selected, the hand held laser apparatus 10 may be further simplified if the pulsewidth and repetition rate is not desired to be variable. In this instance, the pulsewidth control circuit 34 may be removed such that a direct connection may be provided between the switching means 42 and the semiconductor laser device 14.

In each of these embodiments, a photodetector 36 may be provided within the hand held laser apparatus 10 itself, between the emitting facet of the semiconductor laser device 14 and the focusing and collimating lens 18 in order to detect the output power level 40 of the semiconductor laser device 14. This value, determined by the photodetector 36, may be displayed for the operator such that the power level may be adjusted which in turn alters the current level supplied to the semiconductor laser device 14 so as to adjust the output power level 14 and correct for any deficiencies noted by the photodetector 36.

Similarly, in each of these embodiments, the value of the drive current, if the laser is operated in continuous wave mode, may be determined in any manner known to those skilled in the art and displayed for the operator. A typical method of determining the drive current is by measuring the voltage value across the current sensing resistor and dividing that measurement by the resistive value. The amount of the drive current may be displayed for the operator so that the operator could adjust the input power level to vary the drive current and so that the operator can manually observe that the laser is not receiving excessive current. The pulse width of a pulsed laser output, its repetition rate, and other values may also be measured and displayed for the operator in manners well known to those skilled in the art.

Figure 7:
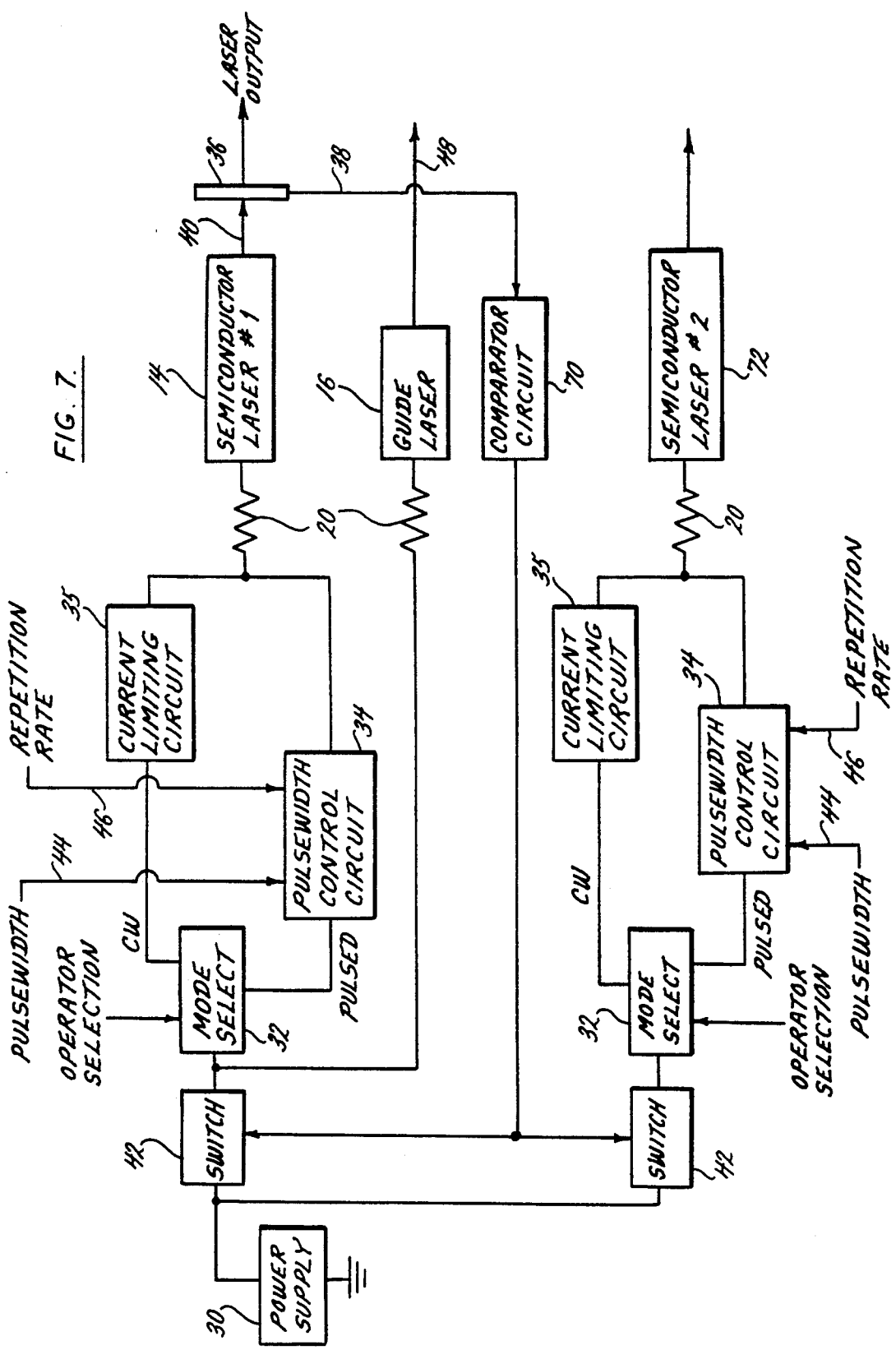
FIG. 7 is a block diagram representation of an alternative embodiment the hand held laser apparatus incorporating the features of this invention.

An alternative embodiment, as shown schematically in FIG. 7, is the utilization of a pair of semiconductor laser devices in addition to the guide laser device 16. In this alternative embodiment, a first semiconductor laser device 14 would operate as previously described in conjunction with the prior embodiments. A photodetector 36, as previously described, would also be utilized and may provide a display 22 of the output power 40 produced by the first semiconductor laser device 14 as previously described. The output 38 of the photodetector 36 in addition to being displayed may be transmitted to a comparator circuit 70 which compares the output 40 of the semiconductor laser device 14 to a predetermined value. In this fashion, should the first semiconductor laser device 14 fail for any reason and its output power level 40 fall below the predetermined minimum level in the comparator circuit 70, the second semiconductor laser device 72 would be switchably connected to the power supply 30 while the first semiconductor laser device 14 is simultaneous disconnected from the power supply 30. This embodiment utilizing a pair of semiconductor laser devices may also be designed for constant power output such that the need for an adjustable power supply is removed. Thus, as previously discussed, the power supply 30 and control circuitry of this embodiment may be packaged in a portable container or may be incorporated within the body of the hand held laser apparatus 10 itself. The apparatus 10 in such an embodiment may be packaged so that it is disposable upon discharge of the batteries, exhaustion of the laser, or its exposure to a contaminated environment.

The operator, in such an instance, would be able to apply a laser output to the workpiece at a constant power level even though the first semiconductor laser device 14 should happen to fail for any reason. This ability to switch to a second semiconductor laser device 70 is particularly important in the medical field in which the hand held laser apparatus 10 may be used during surgery or treatment of a patient whose exposure to the laser in crucial in terms of both power level and duration.

While multiple semiconductor laser devices may be utilized in the alternative to provide redundancy for increased reliability, a plurality of semiconductor laser devices could also be used in parallel to increase the output power of the hand held laser apparatus. Each semiconductor laser would be connected in a similar fashion to the semiconductor laser device described in the initial embodiment. While multiple, individual semiconductor lasers may be utilized to increase the operating power level of the device, as semiconductor laser array could be used as well such that the individual emitters of the array could be combined in to an output beam of increased power. Additionally, a plurality of semiconductor laser devices could be utilized, each of which has a different lasing wavelength. The semiconductor laser devices could then be connected, as previously described, with the addition of an additional switch with which the operator could select the output wavelength desired. In this fashion, a laser output of various wavelengths could be produced by a single hand held laser apparatus. The additional switch could be connected such that the operator could select multiple wavelengths such that several semiconductor laser device were energized simultaneously so as to have mixed wavelengths in the lasers' output.

While the hand held laser apparatuses 10 have been described in conjunction with medical applications, such hand held laser apparatuses 10 could also be utilized in numerous other applications such as industrial processing as well as imaging and tracking applications.

Although there has been illustrated and described a specific detail and structure of operations, it is clearly understood that the same were merely for purposes of illustration and that changes and modifications may be readily made therein both those skilled in the art without departing from the spirit and scope of the invention.

We claim:

1. A hand held laser apparatus, comprising:
    a) a substantially elongated, hollow housing;
    b) a first semiconductor laser means for producing a light output, wherein the semiconductor laser means is electrically connected to a power supply means, the semiconductor laser means being disposed within the housing;
    c) a guide laser means for producing a visible light output, wherein the guide laser means is electrically connected to the power supply means, the guide laser means being disposed within the housing;
    d) a collimating lens means for collimating the output of the semiconductor laser means and the guide laser means; and e) a focusing lens means for focusing, upon a workpiece, the output of the semiconductor laser means and the guide laser means.

2. A hand held laser apparatus as recited in claim 1, further comprising a switching means interdisposed between the power supply means and both the semiconductor laser means and the guide laser means such that the power supply means may be electrically disconnected from the semiconductor laser means and the guide laser means.

3. A hand held laser apparatus as recited in claim 2, further comprising a mode select control means for allowing an operator to select between a continuous wave mode and a pulsed mode wherein the mode select control means provides for a continuous electrical connection between the power supply and the semiconductor laser means upon the selection of the continuous wave mode and wherein the mode select control means provides for an intermittent electrical connection between the power supply means and the semiconductor laser means upon the selection of the pulsed mode.

4. A hand held laser apparatus as recited in claim 3, further comprising a pulsewidth control means, activated only upon the selection by the operator of the pulsed mode, for allowing an operator to select a desired pulsewidth for an output pulse of light from the semiconductor laser device and a desired repetition rate for the pulses of output light from the semiconductor laser device, the pulsewidth control means regulating the intermittent electrical connection between the power supply means and the semiconductor laser means such that an electrical connection is only maintained for a time equal to the selected pulsewidth with the electrical connection repeated at a rate equal to the repetition rate selected.

5. A hand held laser apparatus as recited in claim 4 wherein the housing has a first end having a conical structure, the collimating lens means are the focusing lens means being disposed within the first end.

6. A hand held laser apparatus as recited in claim 5, further comprising a photodetecting means for measuring the output power level of the light output of the semiconductor laser means.

7. A hand held laser apparatus as recited in claim 6, further comprising a display means for displaying the output power level measured by the photodetecting means of the light output of the semiconductor laser means.

8. A hand held laser apparatus as recited in claim 5, further comprising:
   a) a first resistive means interdisposed between the power supply means and the semiconductor laser means for limiting current flow to the semiconductor laser means; and
   b) a second resistive means interdisposed between the power supply means and the guide laser means for limiting current flow to the guide laser means.

9. A hand held laser apparatus as recited in claim 4 wherein the housing comprises:
   a) a first section containing the collimating lens means and the focusing lens means at one end thereof; and
   b) a second section for an operator to grasp, the first section and the second section aligned in an angled configuration.

10. A hand held laser apparatus as recited in claim 1, further comprising:
    a) a second semiconductor laser means for producing a light output positioned such that the light output is focused by the focusing lens and collimated by the collimating lens, the second semiconductor laser means being switchably connected to the power supply means, the second semiconductor laser means being disposed within the housing.
    b) a switching means interdisposed between the power supply means and both the first and second semiconductor laser means and the guide laser means such that the power supply means may be electrically disconnected from the first and second semiconductor laser means and the guide laser means;
    c) a photodetecting means for measuring the output power level of the light output of the first semiconductor laser means; and
    d) a comparator means for comparing the power level measured by the photodetecting means to a predetermined power level, the comparator means controlling the switching means such that either the first semiconductor laser means and the guide laser means are connected and the second semiconductor laser means is disconnected from the power supply means if the output power level is greater than or equal to the predetermined power level or the second semiconductor laser means and the guide laser means are connected and the first semiconductor means is disconnected from the power supply means if the output power level is less than the predetermined power level.

11. A hand held laser apparatus as recited in claim 10, further comprising a first and a second mode select control means for allowing an operator to select between a continuous wave mode and a pulsed mode, the first mode select control means, upon the selection of the continuous wave mode, provides for a continuous electrical connection between the power supply and the first semiconductor laser means if the first semiconductor laser means is switchably connected to the power supply, the first mode select control means, upon the selection of the pulsed mode, provides for an intermittent electrical connection between the power supply means and the first semiconductor laser means if the first semiconductor laser means is switchably connected to the power supply, the second mode select control means, upon the selection of the continuous wave mode, provides for a continuous electrical connection between the power supply and the second semiconductor laser means if the second semiconductor laser means is switchably connected to the power supply, and the second mode select control means, upon the selection of the pulsed mode, provides for an intermittent electrical connection between the power supply means and the second semiconductor laser means if the second semiconductor laser means is switchably connected to the power supply.

12. A hand held laser apparatus as recited in claim 11, further comprising a first and second pulsewidth control means, activated only upon the selection by the operator of the pulsed mode, for allowing an operator to select a desired pulsewidth for an output pulse of light from the semiconductor laser device and a desired repetition rate for the pulses of output light from the semiconductor laser device, the first pulsewidth control means regulating the intermittent electrical connection between the power supply means and the first semiconductor laser means if the first semiconductor laser means is switchably connected to the power supply such that an electrical connection is only maintained for a time equal to the selected pulsewidth with the electrical connection repeated at a rate equal to the repetition rate selected, and the second pulsewidth control means regulating the intermittent electrical connection between the power supply means and the second semiconductor laser means if the second semiconductor laser means is switchably connected to the power supply such that an electrical connection is only maintained for a time equal to the selected pulsewidth with the electrical connection repeated at a rate equal to the repetition rate selected.

13. A hand held laser apparatus as recited in claim 12, further comprising a third resistive means interdisposed between the power supply means and the second semiconductor laser means for limiting current flow to the second semiconductor laser means.

14. A hand held laser apparatus as recited in claim 13, further comprising a display means for displaying the output power level measured by the photodetecting means of the light output of the semiconductor laser means.

15. A hand held laser apparatus, comprising:
 a) a substantially elongated, hollow housing;
 b) a first semiconductor laser means for producing a light output wherein the semiconductor laser means is electrically connected to a power supply means, the first semiconductor laser means being disposed within the housing;
 c) a guide light emitting diode means for producing a visible light output wherein the guide light emitting diode means is electrically connected to the power supply means, the guide light emitting diode means being disposed within the housing;
 d) a first collimating lens means for collimating the output of the semiconductor laser means;
 e) a first focusing lens means for focusing, upon a workpiece, the output of the semiconductor laser means;
 f) a second collimating lens means for collimating the output of the guide light emitting diode means; and
 g) a second focusing lens means for focusing, upon a workpiece, the output of the guide light emitting diode means.

16. A hand held laser apparatus, comprising:
 a) a substantially elongated, hollow housing;
 b) a plurality of semiconductor laser means for producing a light output wherein the plurality of semiconductor laser means are electrically connected to a power supply means, the plurality of semiconductor laser means being disposed within the housing;
 c) a guide laser means for producing a visible light output wherein the guide laser means is electrically connected to the power supply means, the guide laser means being disposed within the housing;
 d) a collimating lens means for collimating the output of the plurality of semiconductor laser means and the guide laser means; and
 e) a first focusing lens means for focusing, upon a workpiece, the output of the plurality of semiconductor laser means and the guide laser means.

17. A hand held laser apparatus, as recited in claim 16, wherein the plurality of semiconductor laser means are connected to the power supply means such that the operator may switchably select the particular semiconductor laser means to energize.

18. A hand held laser apparatus, as recited in claim 17, wherein each semiconductor laser means of the plurality of semiconductor laser means produces an output having a substantially different wavelength from the wavelength of light produced by the other semiconductor laser means.

19. A hand held laser apparatus, comprising:
 a) a substantially elongated, hollow housing;
 b) a semiconductor laser array means for producing a light output wherein the semiconductor laser array means are electrically connected to a power supply means, the semiconductor laser array means being disposed within the housing;
 c) a guide laser means for producing a visible light output wherein the guide laser means is electrically connected to the power supply means, the guide laser means being disposed within the housing;
 d) a collimating lens means for collimating the output of the semiconductor laser array means and the guide laser means; and
 e) a first focusing lens means for focusing, upon a workpiece, the output of the semiconductor laser array means and the guide laser means.

* * * * *